US012508150B2

(12) United States Patent
Young et al.

(10) Patent No.: US 12,508,150 B2
(45) Date of Patent: Dec. 30, 2025

(54) OSTOMY POUCH

(71) Applicant: ConvaTec Limited, Flintshire (GB)

(72) Inventors: Alice Young, Flintshire (GB); Sabrina Falloon, Flintshire (GB); Kevin Evans, Flintshire (GB)

(73) Assignee: CONVATEC LIMITED, Flintshire (GB)

(*) Notice: Subject to any disclaimer, the term of this patent is extended or adjusted under 35 U.S.C. 154(b) by 840 days.

(21) Appl. No.: 17/335,446

(22) Filed: Jun. 1, 2021

(65) Prior Publication Data

US 2021/0369493 A1 Dec. 2, 2021

Related U.S. Application Data

(63) Continuation of application No. PCT/GB2021/051337, filed on Jun. 1, 2021.

(30) Foreign Application Priority Data

Jun. 2, 2020 (GB) ..................................... 2008256

(51) Int. Cl.
*A61F 5/44* (2006.01)
*A61F 5/445* (2006.01)

(52) U.S. Cl.
CPC ............ *A61F 5/4407* (2013.01); *A61F 5/445* (2013.01)

(58) Field of Classification Search
CPC .... A61F 5/443; A61F 5/445; A61F 13/00085; A61F 13/0259; A61F 2013/008; A61F 5/4407
See application file for complete search history.

(56) References Cited

U.S. PATENT DOCUMENTS 3,902,496 A * 9/1975 Eakin ...................... A61F 5/445 604/334
4,233,977 A * 11/1980 Mattson ................ A61F 5/4407 604/335

(Continued)

FOREIGN PATENT DOCUMENTS

EP 3096719 B1 2/2022
EP 3755285 B1 5/2022

(Continued)

OTHER PUBLICATIONS

International Search Report; European Patent Office; International Application No. PCT/GB2021/051337; Sep. 16, 2021; 3 pages.

(Continued)

*Primary Examiner* — Ariana Zimbouski
*Assistant Examiner* — Alessandro R Del Priore
(74) *Attorney, Agent, or Firm* — TAFT STETTINIUS HOLLISTER LLP; Ryan O. White; Derek B. Lavender

(57) ABSTRACT

The invention relates to an ostomy pouch 10. The pouch 10 includes inner and outer walls 18*b*, 20*b* of flexible sheet material which sealed about a periphery. The walls 18*b*, 20*b* define a cavity for containing a stomal output and a drain 32 for draining stomal output from the cavity. An opaque comfort layer 18*a*, 20*a* is provided, at over an outer surface of the inner and/or outer walls 18*b*, 20*b*. The drain 32 is moveable between a deployed position for draining the stomal output from the cavity and a stowed position for storage of the drain 32, with at least part of the drain 32 overlying a portion of the comfort layer 18*a*, 20*a* in the stowed position. The drain 32 is substantially opaque on one side, and at least partly transparent on an opposing side.

17 Claims, 10 Drawing Sheets

(56) References Cited

U.S. PATENT DOCUMENTS

| | | | | |
|---|---|---|---|---|
| 6,186,989 | B1 * | 2/2001 | Horie | A61F 5/449 604/345 |
| 11,039,950 | B2 | 6/2021 | Jones, Jr. et al. | |
| 11,793,662 | B2 | 10/2023 | Hoggarth et al. | |
| 11,826,277 | B2 | 11/2023 | Tan | |
| 2004/0049837 | A1 * | 3/2004 | Falconer | A61F 5/4407 383/88 |
| 2005/0131360 | A1 * | 6/2005 | Villefrance | A61F 5/445 604/332 |
| 2005/0159717 | A1 * | 7/2005 | Holtermann | A61F 5/4407 604/332 |
| 2008/0300556 | A1 * | 12/2008 | Fenton | A61F 5/4404 604/339 |
| 2011/0028923 | A1 * | 2/2011 | Murray | A61F 5/4405 604/332 |
| 2011/0028924 | A1 * | 2/2011 | Murray | A61F 5/4407 604/332 |
| 2013/0053802 | A1 * | 2/2013 | Maidl | A61F 5/445 604/332 |
| 2013/0253455 | A1 * | 9/2013 | Masters | A61F 5/445 604/332 |
| 2014/0039430 | A1 * | 2/2014 | Richmann | A61F 5/443 604/332 |
| 2018/0333290 | A1 * | 11/2018 | Jones | A61F 5/441 |
| 2021/0244564 | A1 | 8/2021 | Jones, Jr. et al. | |
| 2021/0369491 | A1 | 12/2021 | Holden | |
| 2022/0117772 | A1 | 4/2022 | Tan | |

FOREIGN PATENT DOCUMENTS

| | | | |
|---|---|---|---|
| EP | 4037622 | A1 | 8/2022 |
| EP | 4037623 | A1 | 8/2022 |
| EP | 4037625 | A1 | 8/2022 |
| EP | 4037626 | A1 | 8/2022 |
| EP | 3755284 | B1 | 10/2023 |
| EP | 4257099 | A1 | 10/2023 |
| EP | 3393410 | B1 | 3/2024 |
| EP | 3544554 | B1 | 4/2024 |

OTHER PUBLICATIONS

Written Opinion of the International Searching Authority; European Patent Office; International Application No. PCT/GB2021/051337; Sep. 16, 2021; 7 pages.

* cited by examiner

OSTOMY POUCH

This application is a continuation of International Application No. PCT/GB2021/051337 filed Jun. 1, 2021 and claims the priority of foreign Application No. GB2008256.6 filed Jun. 2, 2020. The disclosures of which are hereby incorporated herein in their entirety.

TECHNICAL FIELD OF THE INVENTION

The present invention relates to an ostomy pouch, and in particular to an ostomy pouch which is drainable.

BACKGROUND TO THE INVENTION

An ostomy pouch may be used to collect and hold stomal output from a stoma formed in the body of an ostomate. Generally the stoma is a surgical opening in the torso of the ostomate's body, but may also refer to internal tissue, organs or portions thereof that are exposed by the opening. Ostomy pouches typically take the form of a pair of walls sealed together to form a cavity into which stomal output may be expelled from the ostomate through a formed stoma.

Given the nature and use of ostomy pouches, it is desirable for a pouch to be able to be worn by an ostomate as easily and discreetly as possible. It is also advantageous for the pouch to be worn for an extended period of time for increased convenience for the ostomate. For this reason, some ostomy pouches may be provided with a drain allowing the ostomate to intermittently drain stomal output from the cavity. Drains are typically moveable in some manner (e.g. by folding and/or rolling) between a stowed position where the pouch is closed, and a deployed position wherein the drain is open allowing the contents of the pouch to be drained therefrom—e.g. by opening a drain aperture in the pouch.

It may be desirable for a user for the contents of the ostomy pouch to be concealed during normal use. Accordingly, pouches are generally made from an opaque material and/or have an opaque cover or "comfort" layer overlying the walls of the pouch. However, it is also desirable for the ostomate/user to be able to view the contents of the pouch, or at least the stomal output passing through the drain of the pouch, during draining to provide greater control over the process.

Accordingly, some known solutions include ostomy pouches which are substantially opaque, with a transparent drain section which allows the user to view the stomal output being expelled through the drain when draining the pouch. However, many current solutions result in the output within the pouch being partly visible through transparent sections of the pouch (e.g. the drain), even where the drain is stowed/folded. In further solutions, such as that used in the Esteem®+Convex Invisiclose Drainable Pouch with Lock-it Pocket™ pouch by ConvaTec, arrangements have been provided which have an additional layer, or plurality of layers of comfort material arranged at the base of the pouch, forming a pocket, so as to allow for the drain to be folded up, then hidden when then the pocket is inverted. Whilst the primary purpose is to provide means to secure the drain in a stowed position, such an arrangement may also be used to conceal any visible transparent portions of the pouch with the drain stowed. However, such pouches require additional manufacturing steps and suffer from increased complexity from a usability point of view, and in some instances may require the ostomate to use two hands to fully stow (and conceal) the drain. For example the Lock-it Pocket™ is closed by placing the thumbs into the bottom corners of the Lock-it Pocket™ and turning it inside out, as if closing a money bag, to hold drain securely. Whilst this certainly improves discretion and security, the product still has a flat base, which takes its shape from the shape of the folded-up drain and is thus identifiable as drainable devices (which is considered an undesirable characteristic as the draining process is considered somewhat unpleasant).

It is an aim of an embodiment or embodiments of the invention to overcome or at least partially mitigate one or more problems with the prior art.

SUMMARY OF THE INVENTION

According to an aspect of the invention there is provided an ostomy pouch, comprising: inner and outer walls defining: a cavity for containing a stomal output; and a drain for draining stomal output from the cavity; a comfort layer provided, at least in part over an outer surface of the inner and/or outer wall of the cavity; and a fastener arrangement configured to retain the drain in a stowed position, the fastener arrangement comprising a first fastener located on the comfort material and a second fastener provided on the inner wall or outer wall of the ostomy pouch; wherein at least a portion of the inner wall defining the drain is substantially opaque and at least a portion of the outer wall defining the drain is at least partly transparent.

According to an aspect of the invention there is provided an ostomy pouch, comprising: inner and outer walls of flexible sheet material sealed about a periphery thereof to define: a cavity for containing a stomal output; and a deployable drain for draining stomal output from the cavity; a substantially opaque comfort layer provided, at least in part over an outer surface of the inner and/or outer walls of the flexible sheet material; and a fastener arrangement configured to retain the deployable drain in the stowed position, the fastener arrangement comprising a first fastener located on an outer surface of the comfort material and a second fastener provided on the inner wall or outer wall of the ostomy pouch; wherein the deployable drain is moveable between a deployed position for draining the stomal output from the cavity and a stowed position for storage of the deployable drain, with at least part of the drain overlying a portion of the comfort layer in the stowed position; and wherein at least a portion of the inner wall defining the deployable drain is substantially opaque and at least a portion of the outer wall defining the deployable drain is at least partly transparent.

Advantageously, the ostomy pouch of the present invention may permit an ostomate to increase the period of use of the pouch by providing means for draining the cavity of stomal output reliably and hygienically. Since the ostomate may be inclined to use each ostomy appliance of the present disclosure for longer, the total number of ostomy appliances used by the ostomate in a given time period may be reduced. This may produce an environmental benefit in reducing the amount of environmental waste produced. The provision of a drain which is at least partly transparent on one side, specifically the outer wall side allows the ostomate or user to view the contents of the pouch whilst draining. Having the drain being substantially opaque on one side, specifically the inner wall side, and a fastener located on a comfort material overlaid one or both walls of the pouch ensures the contents of the pouch are concealed with the drain stowed by having the drain moveable to a stowed position overlying the comfort material.

Optional features set out below may apply to any aspect of the invention as appropriate.

The drain may comprise an elongate extension of the inner and outer walls. The inner and outer walls may together define an elongate drain channel which extends from a drain inlet at the cavity and a drain aperture at a distal end of the drain channel through which stomal output from within the cavity can be drained from the pouch.

The inner and outer walls may be sealed (e.g. welded) about the periphery thereof to define the cavity and/or the drain. The seal/weld may comprise a single continuous edge seal. The single continuous edge seal may extend from a first edge (e.g. a left-hand edge) of a drain channel to a second edge (e.g. a right-hand edge) of a drain channel of the pouch. The single continuous edge seal may comprise a weld, which may optionally have a width of between 2 mm to 6 mm, or between 3 mm to 5 mm, or approximately 4 mm, for example. The single continuous edge seal may have a constant width around the periphery of the ostomy pouch.

The deployable drain may be moveable between stowed and deployed positions by rolling or folding the drain, for example, about one or more fold lines in the drain. The drain may be moved, in use, from the deployed position to the stowed position by folding and/or rolling the drain in a direction which is upwards and away from the ostomate.

In embodiments, the first fastener may comprise a strip of hook fasteners and the second fastener may comprise a strip of loop fasteners together forming a hook and loop fastener arrangement. Equally, the second fastener may comprise a strip of loop fasteners and the first fastener may comprise a strip of hook fasteners. The first and second fasteners may each comprise a strip of hook fasteners forming a dual hook fastener arrangement.

The second fastener may be located on the inner wall of the pouch. In embodiments, the second fastener is located on a portion of the inner wall of the pouch at least partly defining the drain. Advantageously, as the drain is stowed (e.g. by rolling or folding the drain upwards and away from the ostomate in use) a fastener located on the inner wall of the pouch (i.e. the second fastener) may be brought proximal to a fastener (i.e. the first fastener) located on an outer surface (i.e. the comfort layer) of the pouch.

The first fastener may comprise a flap, which itself may be secured (e.g. adhesively, for example using an adhesive tape, welded or otherwise) to comfort layer of the pouch. For example, in some embodiments the first fastener may comprise a strip of hook or loop fasteners provided on a flap secured to an outer surface of the comfort layer. The flap may comprise a flexible material, e.g. a flexible plastics material.

The comfort material may be a non-woven layer or a woven layer. If a woven layer, the woven layer may comprise a hot-melt adhesive (e.g. a web of EVA) in the region of the flap to aid the bonding of the flap to the comfort material, for example in a welding operation. The hot-melt adhesive may be arranged on the inside surface of the woven layer, with the flap applied to the outside layer. The hot-melt adhesive may penetrate the woven layer in the welding process to improve the bond between the flap and the woven comfort layer. The entire inside surface of the comfort material to which the flap is bonded may be coated in a web of hot-melt adhesive. The web may have a mass of adhesive with voids therein, so as to reduce the amount of material required.

The flap may be provided on a comfort layer which overlies the outer wall of the pouch, away from the ostomate, in use.

The flap may be shaped so as to correspond to one or more contours of the ostomy pouch. For example, in some embodiments the pouch may comprise one or more curved edges, and the flap may be similarly curved to correspond the contours of the curved edge(s) of the pouch. The flap may be wider than the drain. The flap may extend across substantially the entire width of the pouch. This can better obscure the folded drain than a flap attached to the drain itself. The flap may extend up to the edge of the pouch, or may extend up to the seal about the periphery of the pouch. In some embodiments, where the flap extends up to the seal, it may be adhered or welded to the pouch. In some embodiments, where the flap extends up to the edge of the pouch it may be adhered to the pouch, for example using adhesive tape. Advantageously, the flap may extend a maximum distance across the width of the pouch without interfering with the sealed periphery of the pouch. Having a flap, rather than an invertible pocket to cover the drain allows the shape of the base to be designed as desired, not dictated by the shape of the folded drain, so the fact that the product is drainable may be less obvious. Moreover, closing a flap can be easier e.g. with one hand or by users with lower manual dexterity than closing a pocket.

The drain may comprise one or more pursing strips. The pursing strips may comprise a rigid, bendable material. The pursing strip(s) may be associated with the inner or outer wall of the pouch. For example, the pursing strips may be adhesively or otherwise fixed to the inner or outer wall of the pouch. The pursing strip(s) may assist in separating the inner and outer walls of the pouch, in a portion thereof, to define a drain aperture in the pouch for draining stomal output from the cavity. For example, in use, the pursing strips may bend or arch under the application of a force by the ostomate/user. The bending or arching the strips may cause a corresponding movement of the inner and/or outer walls of the pouch to define an opening (i.e. a drain aperture) within the pouch.

In embodiments, the drain may comprise a pair of pursing strips. The pair of pursing strips may be provided on opposing sides of the drain. For example, the drain may comprise a first pursing strip on the inner wall and a second pursing strip on the outer wall. The pursing strips may overlie one another. Alternatively, the pursing strips may be offset.

The pursing strip(s) may be substantially rectangular in shape, and may have one or more curved corners. In some embodiments the pursing strip(s) may include one or more cut out portions or notches which define an interaction region for the user—i.e. a region where the user may apply a force to the strip(s) in use to bend/arch the strip(s). For example, the pursing strip(s) may include a pair of opposing cut out regions/notches. In embodiments comprising a pair of pursing strips, each of the pursing strips may comprise one or more cut out portions or notches, and which may optionally be aligned with (where the strips overlie one another) or positioned adjacent to (where the strips are offset from one another) a corresponding cut out region or notch in the other pursing strip. Advantageously, the cut out region(s)/notch(es) in the pair of pursing strips may together define an interaction region for the user.

In embodiments, the drain may be sub-divided into two or more segments. The segments may be defined by fold lines about which the drain may be folded when moving between deployed and stowed positions. For example, the drain segments may be sequentially folded to overlie one another in moving from the deployed position to the stowed position. The drain may comprise at least two segments, with a first pursing strip positioned on the inner wall of the pouch and defining, at least in part a first segment of the drain, with a second pursing strip positioned on the outer wall of the pouch and defining, at least in part a second segment of the drain. The drain may be sub-divided into three segments, with the second fastener provided on the inner wall of the pouch and defining, at least in part, a third segment of the drain.

At least a portion of the deployable drain may be visible in the stowed position. For example, in the stowed position the deployable drain may be partly covered by the flap, but may also have one or more portions which remain uncovered and thereby visible, in use. The or each portion visible in the stowed position may comprise a region or regions of the drain at or proximal to one or more edges, optionally one or more lateral edges, of the drain. The or each portion visible in the stowed position may preferably comprise a portion of the opaque inner wall of the pouch defining the drain.

The drain may be provided in a lower section of the pouch, e.g. where the pouch is configured to be used in a substantially vertical orientation.

The inner wall of the pouch may comprise an inlet for receiving the stomal output into the cavity. In presently preferred embodiments, the inlet is provided within a portion of the inner wall defining at least part of an upper section of the pouch.

The flexible sheet material of the inner and outer walls may comprise a single layer or a laminate of a plurality of layers. The flexible sheet material of the inner wall and/or the outer wall may comprise polyvinylidene chloride (PVDC) and/or ethylene-vinyl acetate (EVA). The inner wall and/or the outer wall may have a thickness of between 50 to 150 micrometres, or between 75 to 125 micrometres, or between 75 to 100 micrometres, for example.

The comfort layer may be formed from a flexible sheet material. The material of the flexible sheet material may comprise one or more of polyester, nylon, viscose, polyurethane, polyethylene, polypropylene, polyvinylidene chloride (PVDC) and ethylene-vinyl acetate (EVA). The comfort layer may comprise a laminate of two or more layers. The comfort layer may comprise at least one fabric layer and at least one film layer. The at least one film layer may be laminated to the at least one fabric layer, and optionally may be laminated to the at least one fabric layer over an entire area of the at least one comfort layer. The at least one fabric layer may comprise a woven or a non-woven textile layer. The fabric layer may comprise polyester, nylon, viscose, polyethylene or polypropylene. The at least one film layer may comprise polyurethane, polyvinylidene chloride (PVDC) or ethylene-vinyl acetate (EVA). The comfort layer may have a thickness of between 50 to 1000 micrometres, or between 60 to 500 micrometres, or between 75 to 300 micrometres, or between 100 to 200 micrometres, for example.

The pouch may comprise an inner comfort layer and/or an outer comfort layer. The inner comfort layer may overlie at least a portion of the inner wall of the pouch. The outer comfort layer may overlie at least a portion of the outer wall of the pouch. The comfort layer(s) (e.g. the inner and/or outer comfort layers) may not overlie the inner or outer walls of the pouch at the portions of the inner and/or outer walls which define the drain.

Where present, the outer comfort layer may comprise a first part and a second part which may be joined to the outer wall so that the first part partially overlaps the second part in an overlap region. The first part and the second part may be separable from each other in the overlap region to form a window opening for viewing the cavity. The overlap region may be angled to extend horizontally when the pouch is in use. The first part and the second part of the outer comfort layer may be configured to slide over each other in the overlap region to accommodate expansion of the underlying outer wall. The first part and the second part may be joined to each other at a first end and at a second end of the overlap region. The first part and the second part may be welded to each other at the first end and at the second end of the overlap region, optionally as part of a peripheral weld of the pouch. External edges of the one or more parts of the outer comfort layer are shaped and sized to correspond to the shape, form and contours of the outer wall.

Where present, the inner comfort layer may comprise a single part or multiple parts. The inner comfort layer may cover only a portion of the inner wall. However, preferably the inner comfort layer covers substantially the whole of the inner wall. An aperture may be provided in the inner comfort layer corresponding to the location of the inlet in the inner wall of the pouch. The inner comfort layer may be shaped and sized to correspond to the shape, form and contours of the inner wall. The inner comfort layer may be provided with a wafer aperture that corresponds to the location of the inlet of the inner wall to permit fluid connection of the inlet of the inner wall to an ostomy wafer.

The inner wall and the inner comfort layer may be joined together around their peripheral edges and/or the outer wall and the outer comfort layer may be joined together around their peripheral edges. The joining may be by use of welding, adhesive or equivalent means. A single joining operation may be used to join the inner comfort layer, the inner wall, the outer wall and the outer comfort layer together. For example a single weld may be used to join the four layers.

The cavity may be a single volume or may be sub-divided into two or more chambers. For example, the two or more chambers may be separated by one or more partitions, wall members, or filter elements, for example. In some embodiments the pouch comprises a separation wall between the inner and outer walls defining the cavity into first and second chambers. The separation wall may comprise a filtering element. The filtering element may be fluid-permeable, and may be operable to filter fluid stomal output from solid stomal output.

The filtering element may include an array of apertures allowing the passage of fluid stomal output therethrough. The apertures may have a diameter of between 0.02 mm to 0.10 mm, or between 0.03 mm to 0.08 mm, or between 0.04 mm to 0.06 mm, or between 0.06 mm to 0.08 mm, or between 0.10 mm to 0.40 mm, for example. The spacing between adjacent apertures in the array may be between 0.80 mm to 2.20 mm, or between 1.00 mm to 2.00 mm, or between 1.25 mm to 1.75 mm, for example. The apertures may extend across at least 50%, or at least 75%, or at least 80%, or at least 90% of the surface of the filtering element. The filtering element may extend across at least the lower half or lower quarter of the cavity, and/or may extend across at least the upper half or upper quarter of the cavity.

In use, the first chamber of the cavity is arranged to receive both fluid and solid stomal output from the ostomate via the inlet in the inner wall. The separation wall is arranged to allow passage of fluid stomal output into the second chamber, retaining the solid stomal output in the first chamber. In embodiments wherein the pouch comprises a filter arrangement, the filter arrangement may further be used to separate gaseous stomal output from fluid stomal output, allowing the gaseous stomal output to be removed from the cavity.

The pouch may comprise either an ostomy wafer that is located within or otherwise associated with the inlet of the inner wall, or a releasable coupling that is located within or is otherwise associated with the inlet of the inner wall. In embodiments, the releasable coupling may be configured for coupling with a body fitment component comprising an ostomy wafer. Where present, the ostomy wafer may extend through an aperture of the inner wall and/or inner comfort layer. The ostomy wafer may be provided with a releasable liner which may be removed by a user prior to securing the pouch to the ostomate, in use.

The pouch may comprise a filter arrangement. The filter arrangement may comprise a vent for venting of gaseous stomal output from the cavity. The filter arrangement may comprise an odour filter. The odour filter may comprise a charcoal or activated carbon filter, for example. The odour filter may be substantially circular or disc shaped. A major face of the circular/disc shaped filter may be open allowing for gaseous stomal output to enter the filter therethrough. The odour filter may comprise a strip filter which may have open ends, for example.

The filter arrangement, or components thereof—e.g. the vent—may be provided within or be associated with the outer wall of the ostomy pouch. For example, in some embodiments, the filter arrangement may comprise an odour filter positioned on an exterior surface of the outer wall of the pouch. In such embodiments, the vent may comprise an opening within the outer wall, e.g. a substantially circular opening, positioned proximal to the odour filter and providing a vent through which gaseous stomal output may exit the interior of the pouch and enter the odour filter, in use. Advantageously, having the odour filter exterior to the interior of the pouch may minimise exposure of the filter to stomal output, particularly solid and liquid stomal output which may clog the filter if exposed for an extended period of time, and in doing so may result the pouch to undesirably bloat or balloon. Such an arrangement may be particularly useful for open pouches, for example, where the same pouch may be used for a prolonged period by a user.

In other embodiments the filter arrangement may comprise an odour filter provided on an interior surface of the outer wall of the pouch. In such embodiments, the vent may comprise one or more slits, openings or the like within the outer wall of the ostomy pouch. The slits may be positioned adjacent to the odour filter, for example adjacent to a rear face of the odour filter which is adhered or otherwise coupled to the outer all of the pouch. Whilst suffering the drawbacks of the potential of having the liquid and solid stomal output in contact with the odour filter for extended periods, embodiments wherein the odour filter is provided within the interior of the pouch may provide a cost-effective solution, and may be particularly suited for use with closed pouches, for instance, which are designed for wear for a much shorter period of time when compared with open pouches. Here, the filter may be exposed to the stomal output, but for a much shorter period of time and therefore may be less likely to clog before the end of its use period.

The filter arrangement may comprise a pre-filter. The pre-filter may be configured to control the content of stomal output in contact with the vent and/or odour filter. For example, the pre-filter may be advantageously configured to prevent or at least reduce the level of solid or liquid stomal output able to come into contact with the vent and/or odour filter. The filter arrangement may be provided within or be associated with the outer wall of the ostomy pouch. For example, the vent may comprise one or more slits, openings or the like within the outer wall of the ostomy pouch. The filter arrangement may be provided within, or be associated with an upper section of a pouch, which may be an opposing end of the pouch to the drain.

The filter arrangement may be provided with a filter cap. The filter cap may be provided on an exterior surface of the outer wall of the pouch, or an exterior surface of an outer comfort layer, where present, for example, and may be positioned about an odour filter forming part of the filter arrangement of the pouch. The filter cap may provide protection for the filter arrangement, and in particular may be provided about and be operable to protect an odour filter, in use. The filter cap may include one or more openings or slits therein, e.g. one or more s-slits, which allow for the venting of gas therethrough.

The filter arrangement may additionally include a filter cover label. The filter cover label may comprise a removeable component which may be positioned over the filter cap, in use, to seal the openings/slits therein. This may be particularly useful, for example, where an ostomate plans to swim, bathe or shower. The label may prevent ingress of water through said openings/slits in the cap and thereby prevent clogging of the odour filter from water.

In embodiments, the cavity may comprise one or more sections, for example and upper and a lower section. The cavity may comprise a waisted section located between the upper and lower sections. The waisted section may comprise a minimum width which is less than the maximum width of the upper and/or lower sections.

In embodiments, the cavity may comprise the upper section, the lower section and the waisted section located between the upper section and the lower section.

The maximum widths of the upper and lower sections may be equal (or substantially equal). The maximum width of the upper and lower sections may be different. For example, in some embodiments the maximum width of the upper section may be greater than the maximum width of the lower section.

The maximum width of the upper and/or lower section may be between 120 mm to 170 mm, or between 130 mm to 160 mm, or between 135 mm to 150 mm, or between 135-140 mm, or between 140 mm to 145 mm, for example. In an exemplary embodiment, the maximum width of the upper section may be approximately 142 mm, and the maximum width of the lower section may be between 137 mm to 139 mm.

The minimum width of the waisted section may be between 105 mm to 135 mm, or between 110 mm to 130 mm, or between 110 mm to 125 mm, or between 115 mm to 130 mm, or between 120 mm to 135 mm, or between 115 mm to 120 mm, or between 120 mm to 125 mm, or between 125 mm to 130 mm, or approximately 120 mm, for example. In an exemplary embodiment, the minimum width of the waisted section may be approximately 129 mm, 119 mm, or 109 mm.

The minimum width of the waisted section may be between 5 mm to 30 mm less than the maximum width of the lower section, or between 10 mm to 20 mm less than the maximum width of the lower section, or between 15 mm to 20 mm less than the maximum width of the lower section. The minimum width of the waisted section may be between 10 mm to 35 mm less than the maximum width of the upper section, or between 15 mm to 30 mm less than the maximum width of the upper section, or between 20 mm to 25 mm less than the maximum width of the upper section, for example.

The minimum width of the waisted section may be between 75% to 95% of the maximum width of the lower section, or between 80% to 90% of the maximum width of the lower section, or between 83% to 88% of the maximum width of the lower section.

The minimum width of the waisted section may be between 73% to 92% of the maximum width of the upper section, or between 75% to 85% of the maximum width of the upper section, or between 80% to 85% of the maximum width of the upper section.

The pouch may have a length of between 150 mm to 300 mm when the deployable drain is in a deployed position, and/or may have a length of between 200 mm to 240 mm with the deployable drain in a stowed position.

For example, the pouch may have a length of 230 mm to 300 mm when a drain of the ostomy appliance is in an deployed configuration, optionally of 240 mm to 290 mm, optionally a length of 256 mm or 286 mm. The open ostomy appliance may have a length of 180 mm to 240 mm when a drain of the ostomy appliance is in a folded configuration, optionally of 190 mm to 230 mm, optionally 194 mm, 208 mm, 224 mm or 230 mm.

Opposing edges of the waisted section may be concavely-curved. Opposing edges of the waisted section may have a radius of curvature, or a blend of radii of curvature, wherein the or each radii of curvature may be between 20 mm to 60 mm, or between 30 mm to 50 mm, or between 35 mm to 45 mm, for example. The or each radii of curvature may be approximately 40 mm. Alternatively, the left-hand edge and the right-hand edge of the waisted section may each have a radius of curvature, or a blend of radii of curvature, wherein the or each radii of curvature may be between 30 to 80 mm, optionally between 35 mm to 75 mm, optionally between 40 mm to 70 mm, optionally 60 mm Opposing edges of the waisted section may be configured in substantially the same way or form, and may be mirror images of each other, for example.

The upper and/or lower sections may be generally rounded in shape. For example, the upper section may comprise a continuously curved edge that extends from a first edge (e.g. a left-hand edge) of the waisted section to a second edge (e.g. a right-hand edge) of the waisted section. The lower section may comprise a continuously curved edge that extends from a first edge (e.g. a left-hand edge) of the waisted section to a second edge (e.g. a right-hand edge) of the waisted section.

The continuously curved edge of the upper and/or lower sections may be convexly curved. The continuously curved edge of the upper and/or lower sections may be absent any points of inflection or abrupt changes in contour. The continuously curved edge of the upper and/or lower sections may have a radius of curvature, or a blend of radii of curvature, wherein the or each radii of curvature may be between 40 mm to 80 mm, or between 55 mm to 75 mm, or between 60 mm to 73 mm, or between 65 mm to 70 mm, for example.

In embodiments, the upper and/or lower section may be elongated, and may comprise both a rounded portion and a generally rectangular section. The generally rectangular portion may comprise opposing straight edges. The rounded portion may be provided at a position distal from the waisted section. The generally rectangular portion may be provided at a position proximal to the waisted section.

A junction between the upper and/or lower sections and the waisted section may be demarcated by a single point of inflection between a left-hand edge of the upper or lower section and a left-hand edge of the waisted section, and by a single point of inflection between a right-hand edge of the upper or lower section and a right-hand edge of the waisted section.

A location of the minimum width of the waisted section may be at a distance of between 90 mm to 125 mm, or between 95 mm to 120 mm, or between 100 mm to 115 mm, or between 105 mm to 115 mm, or approximately 99 mm, or 109 mm, or 119 mm from an uppermost edge of the ostomy pouch. A location of the minimum width of the waisted section may be at a distance of between 90 mm to 125 mm, or between 95 mm to 120 mm, or between 100 mm to 115 mm from a lowermost edge of the ostomy pouch. The distance may be between 45% to 60% of the length of the pouch, or between 47% to 57% of the length of the pouch, or between 50% to 55% of the length of the pouch.

The pouch may comprise one or more further sections, for example a third section, and/or a fourth section. The one or more further sections may be separated from one or more other sections of the pouch by respective waisted sections. The waisted sections may have a minimum width which is less than the maximum width of the further section(s).

According to an aspect of the invention there is provided a method for collecting stomal output using an ostomy pouch according to any aspect described herein. The method may comprise attaching the ostomy pouch about a stoma of an ostomate. The ostomy pouch may be attached about the stoma through use of an ostomy wafer of the pouch where the pouch comprises a one-piece ostomy pouch. Alternatively, the method may comprise attaching an ostomy wafer of a body fitment component of a two-piece ostomy pouch about the stoma; and attaching a pouch to the body fitment component. The pouch may be attached to the body fitment component before or after the ostomy wafer has been attached about the stoma. Where the ostomy pouch comprises an open or drainable pouch, the method may comprise draining stomal output from the ostomy pouch.

DETAILED DESCRIPTION OF THE INVENTION

In order that the invention may be more clearly understood one or more embodiments thereof will now be described, by way of example only, with reference to the accompanying drawings, of which:

When used herein and throughout the specification, the term "stomal output" refers to any gases, liquids or solids produced by an ostomate that may be secreted from a stoma or that exit a stoma of the ostomate. The stomal output may comprise gaseous, fluid, liquid and/or solid stomal output.

The term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

The term "ostomate" refers to a subject that may have use of the ostomy pouch described herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

Ostomy pouches disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, a ureterostomy, or a vesicostomy. The ostomy pouches disclosed herein may be used with additional devices including, but not limited to, a shunt, a catheter, a plug or a faecal management system.

In this specification locations and orientations of features may be described with reference to the ostomy pouch being "in use", "orientated as it would be in use" or similar. Such terms refer to the intended orientation of the ostomy pouch when it is adhered or otherwise secured to a body of an ostomate, e.g. with the ostomate in a standing position, irrespective of whether the ostomy pouch is currently performing such a use or the actual position of the ostomate. The terms "upper" and "lower" and related terms refer to the relative position of a part or portion of the ostomy pouch when orientated as it may be in use. For example, a section of the ostomy pouch may be referred to as an "upper" section of the ostomy pouch. In such an example, said section will be intended to be the uppermost section (in the vertical direction) of the ostomy pouch when attached to the body of a standing ostomate. However the reader skilled in the art will appreciate that before attachment to the ostomate said section may not always be the uppermost section and in addition when attached the section may not always be the uppermost section if the ostomate adopts a non-standing position, for example lying down.

Figure 1A:
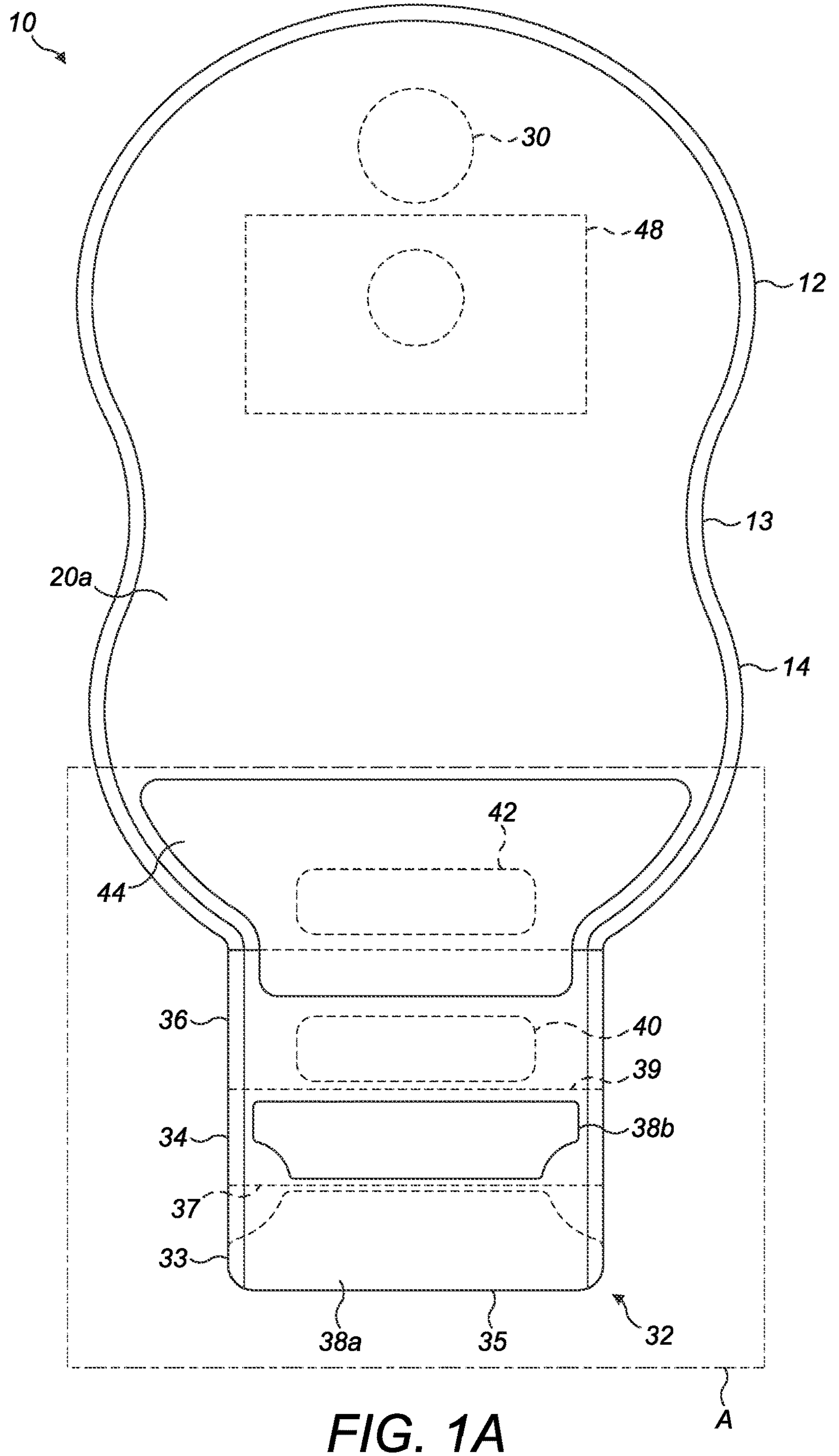
FIG. 1A is a side perspective view of an embodiment of an ostomy pouch in accordance with the invention, illustrating a drain of the ostomy pouch in a deployed position.

The terms "left-hand" and "right-hand" and related terms may refer to the ostomy pouch when viewed from the rear (for example, as shown in FIG. 1A). Thus, as an illustrative example, a "left-hand" edge of the ostomy appliance will be towards a left-hand side of the ostomate in the situation where the ostomy pouch is attached to the front torso of the ostomate.

The terms "concave" and "convex" and related terms refer to shaping of features of the ostomy pouch when viewed from an exterior of the ostomy pouch. Thus, as an illustrative example, an ostomy wafer of circular shape would be considered to have a convexly shaped peripheral edge.

The terms "inner" and "outer" refer to the relative position of a part or portion of the ostomy pouch with reference to the body of an ostomate when the ostomy pouch is attached (e.g. adhesively or otherwise) to the body of the ostomate. "Inner" refers to a position relatively closer to the body of the ostomate than a comparative position that is "outer". "Outer" refers to a position relatively further away from the body of the ostomate than a comparative position that is "inner".

Ostomy pouches are commonly attached to the body of an ostomate by means of an ostomy wafer which includes an adhesive layer or layers. The ostomy wafer typically has an opening for the stoma sometimes referred to as a starter hole which may be cut to a required size by a user before attachment. The ostomy wafer typically comprises an adhesive layer on a body-facing side for adhering the ostomy wafer to the body of the ostomate. Typically, a release liner covers a body-facing side of the ostomy wafer that is removed by the user prior to fitting to the skin. In this specification, the term "ostomy wafer" may be used interchangeably with the terms "adapter," "wafer," "baseplate", or "layered adhesive wafer." The "ostomy wafer", "adapter," "wafer," "baseplate", or "layered adhesive wafer" may form a skin barrier between the ostomate and the pouch. In this specification, the term "ostomy wafer" includes ostomy wafers for a "two-piece appliance" and for a "one-piece appliance".

A "two-piece pouch" refers to an ostomy pouch where the ostomy wafer forms part of a separate body fitment component that is attached by a releasable coupling to a pouch. A two-piece pouch permits the body fitment component to be separated from the pouch without damage, so that at least one of the parts continues to be functionally usable. For example, the body fitment component may remain in place on the body of the ostomate. In contrast, a "one-piece pouch" refers to an ostomy pouch where the ostomy wafer is permanently attached to the appliance, to the extent that the ostomy wafer cannot easily be separated without risk of damaging the appliance. A one-piece pouch is intended to be used as an integral unit.

Ostomy pouches may commonly be configured as "closed" pouches or "open" pouches. In this specification a "closed pouch" refers to an ostomy pouch where it is not intended that stomal output is drained from the cavity. Thus, a closed pouch may typically be configured as a one-use, disposable and non-reusable pouch. In this specification an "open pouch" refers to an ostomy pouch where it is possible for the stomal output to be drained from the cavity and the pouch reused. Thus, an open pouch may be configured as a reusable pouch, such that it can be reused and emptied multiple times whilst attached to the body, although this is not essential. In an open pouch the stomal output may be drained intermittently as instigated by an action of the ostomate or may be drained intermittently or continuously due to the cavity being fluidly connected to a drain, for example a night drain line.

The use of a closed pouch or an open pouch may be, in part, due to user preference, but equally either a closed or open pouch may be more suited depending on the particular ostomate's needs, and depending on the position of the stoma for the ostomate. For example, for stomas formed via ileostomy the stomal output may tend to be looser and be easily drainable which may lead to an open pouch being suitable. For stomas formed by colostomy, the stomal output may tend to be more solid and may not be readily drained by a user. In such instances, a closed pouch may be more suited.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

FIGS. 1A to 4B illustrate an ostomy pouch 10, having an inner wall 18*b* and an outer wall 20*b* sealed about at least part of the periphery thereof to define a cavity for containing a stomal output. The pouch 10 is an open pouch, with the seal provided as a single, continuous seal about the perimeter of the pouch 10, except at a drain aperture 35, described in detail hereinbelow. The cavity includes a first, upper section 12 and a second, lower section 14 which are generally rounded in shape with convex curved edges. The upper and lower sections 12, 14 are separated by a waisted section 13 which is narrower in width than upper and lower sections 12, 14. A deployable drain 32 (described in detail below) is provided extending from the lower section 14 of the pouch 10. It will be appreciated that the pouch shape and form of the pouch 10 shown in the Figures is shown as an example only, and other configurations are envisaged and within the scope of the invention.

The inner and outer walls 18*b*, 20*b* are formed of a flexible, plastics sheet material. The pouch 10 also includes inner and outer comfort layers 18*a*, 20*a* which overlie respective inner and outer walls 18*b*, 20*b*. The comfort layers 18*a*, 20*a* are formed of a woven, fabric material and define an outer surface of the pouch 10. In the illustrated embodiment, the inside surfaces of the woven layers are coated with a web of hot-melt adhesive (in the example, EVA), so a single joining operation is able to be used to join the inner comfort layer 18*a*, the inner wall 18*b*, the outer wall 20*b* and the outer comfort layer 20*a* together, here through welding.

The outer comfort layer includes first and second parts 20*a*', 20*a*" which are joined to the outer wall 20*b* so that the first part 20*a* partially overlaps the second part 20*a*" in an overlap region. In use, the first part 20*a* and the second part 20*a*" are separable from each other in the overlap region to form a window opening for viewing the cavity. In the illustrated embodiment, the second part 20*a*" overlies the first part 20*a*', however in some instances the outer comfort layer 20*a* of the pouch 10 may be configured in the opposite sense, with the first part 20*a*' provided overlying the second part 20*a*".

The inner wall 18*b* comprises an opening therein defining a stomal inlet 48 in the pouch 10 for receiving stomal output into the cavity. Here, the stomal inlet 48 is provided within the upper section 12 of the pouch 10. An aperture 46 is provided in the inner comfort layer 18*a* defining a wafer aperture into which an ostomy wafer 24 is located and positioned over the stomal inlet 48, in use.

The ostomy wafer 24 includes a central aperture 22, an adhesive region 28, and a removable release liner 25 for exposing the adhesive region 28 which may subsequently be used to secure the pouch 10 to and about the stoma of the ostomate, in use. A tab 26 is provided on the release liner 25 to assist the user in removing the release liner 25. The ostomy wafer 24 is suitably secured to the inner wall 18*b*, e.g. through use of a further adhesive region. The adhesive region 28 is mouldable to the extent that it may be manipulated to adjust the shape and size the central aperture 22 according to the size and shape of the ostomate's stoma. When used here and throughout the specification, the term "mouldable" is intended to cover a component, here the adhesive region 28, which can be shaped under application of a force (e.g. rolling) by a user. In an alternative arrangement the adhesive region may be configured such that it may be shaped to fit the stoma by a user cutting the region to make the central aperture 22 the required size and shape, for example.

A separation filter 50 is provided within the pouch 10, positioned between the inner and outer walls 18*b*, 20*b*, separating the cavity into two cavity chambers. The separation filter 50 is fluid-permeable, and is operable to filter fluid (i.e. gaseous and liquid) stomal output from solid stomal output. Specifically, and in use, stomal output is received through the stomal inlet 48 into the first chamber of the cavity. This stomal outlet may be both fluid and solid. The separation 50 is arranged to allow passage of fluid stomal output into the second chamber, proximal to the outer wall 20*b*, whilst retaining the solid stomal output in the first chamber, proximal to the inner wall 18*b*. In the illustrated embodiment, the separation filter 50 is shaped and sized substantially the same as the inner and outer walls 18*b*, 20*b*, and is sealed about its periphery (except in a region proximal to the drain 32) to the inner and outer walls 18*b*, 20*b*.

The illustrated embodiment additionally includes a filter system comprising a vent 30 provided in the outer wall 20*b* for venting of gaseous stomal output from the cavity. This can advantageously maximise the capacity of the pouch 10 for receiving liquid and solid stomal output, and prevent "bloating" or "ballooning" of the pouch 10 which may adversely affect discreetness of the pouch 10 in use. The filter system is provided within the upper section 12 of the pouch. The vent 30 is provided with an odour filter (e.g. a charcoal or activated carbon filter) for reducing the release of unpleasant odours from the cavity. Here, the odour filter is substantially circular in shape, although other shapes and forms of odour filter are equally applicable, as will be appreciated. The filter is located on the outer surface of the outer wall 20*b*, proximal to the position of the vent 30 such that gaseous stomal output released through the vent 30 is released from the pouch 10 via the filter.

In the illustrated embodiment, slits 52 are provided in the outer comfort layer 20*a* proximal to the position of the vent 30 such that gaseous stomal output release through the vent 30 is released from the pouch 10. Gas may escape through the gap between the first and second parts 20*a*', 20*a*" and therefore in some instances the slits 52 may not be provided.

As stated above, pouch 10 is an "open" pouch 10 which includes a drain 32 for draining stomal output from the cavity. The drain 32 comprises a drain aperture 35 formed of an unsealed portion of the periphery of the pouch 10, i.e. a region of the periphery of the inner and outer walls 18*b*, 20*b* which is not sealed together. Stomal output may be released from the cavity through the drain aperture 35, in use.

The drain 32 is integral with the inner and outer walls 18*b*, 20*b*, and forms an elongated portion of the pouch 10 which extends downwardly from a lower edge of the lower section 14. The inner and outer comfort layers 18*a*, 20*a* are not provided over the drain 32. Similarly, the separation filter 50 aligns with the inner and outer comfort layers 18*a*, 20*a* does not extend into the drain 32. The separation filter 50 here is not sealed to the inner and outer walls 18*b*, 20*b* at its lowermost edge, allowing for stomal output to drain from both the first and second cavity chambers of the cavity through the drain 32.

Figure 1B:
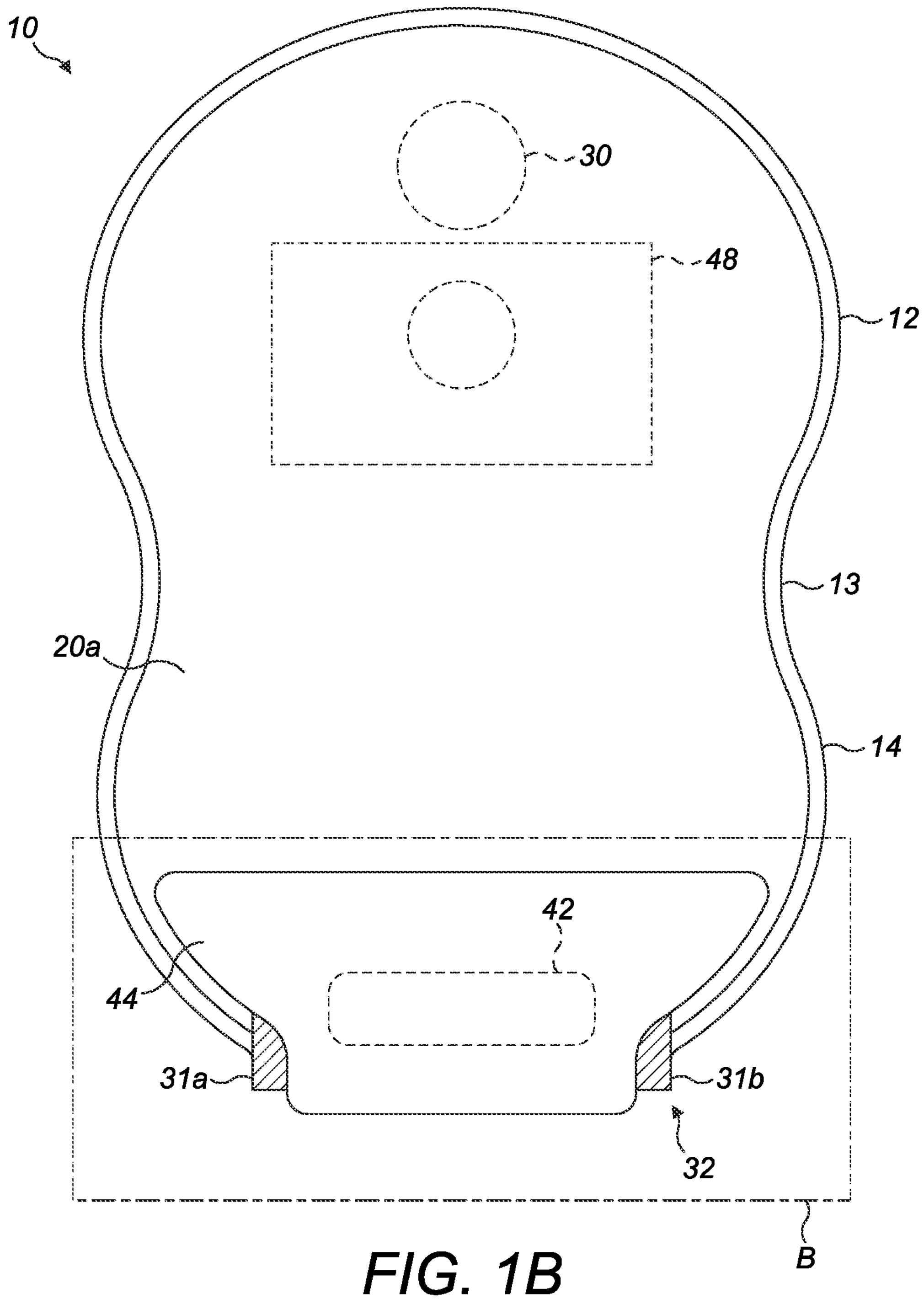
FIG. 1B is a further side perspective view of the ostomy pouch of FIG. 1A, illustrating the drain in a stowed position.
Figure 4A:
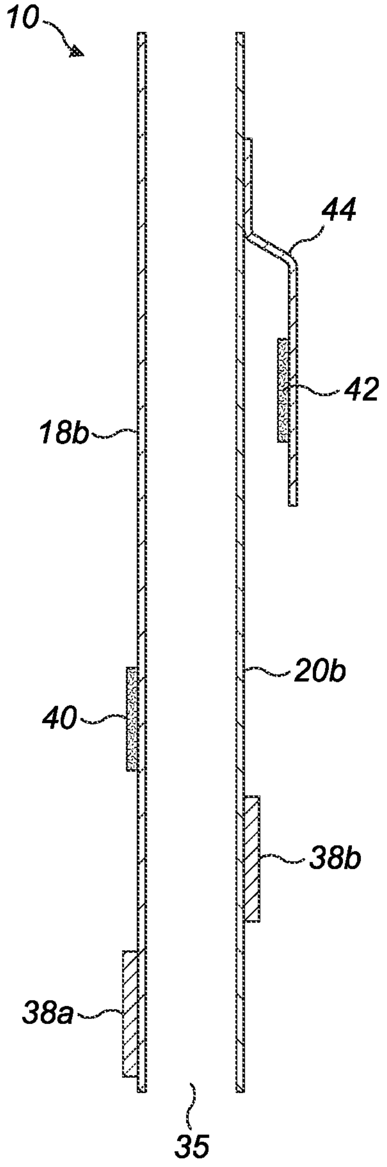
FIG. 4A is a side cross-sectional view of FIG. 2A.
Figure 4B:
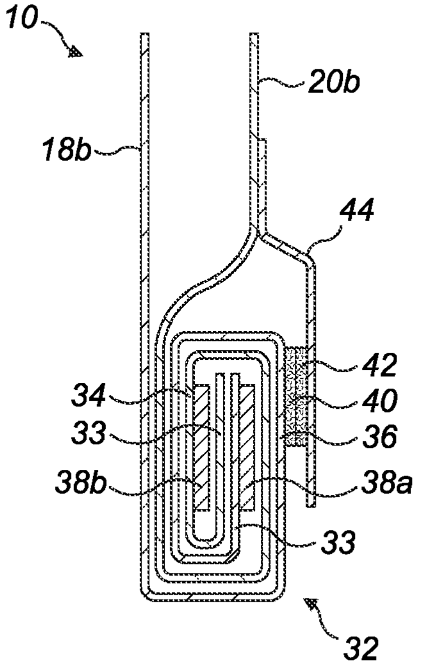
FIG. 4B is a side cross-sectional view of FIG. 2B.

The drain 32 is a deployable drain 32 which is moveable between a deployed position (shown in FIG. 1A) to a stowed position (shown in FIG. 1B). Moving the drain 32 to the stowed position effectively closes off the drain aperture 35 preventing release of stomal output from the cavity. Specifically, the drain 32 is foldable between the deployed and stowed positions roughly about fold lines 37, 39 in the drain 32. The fold lines define the drain 32 into first, second and third segments 33, 34, 36, with the segments 33, 34, 36 being foldable on top of one another, e.g. about fold lines 37, 39 when moving from the deployed position to the stowed position. The relative positions of the first, second and third segments 33, 34, 36 of the drain when in the stowed position is shown in FIG. 4B.

Pursing strips 38*a*, 38*b* are provided on opposing sides of the drain 32, with a first pursing strip 38*a* provided on the portion of the inner wall 18*b* defining the first segment 33 of the drain 32, and a second pursing strip 38*b* provided on the portion of the outer wall 20*b* defining the second segment 34 of the drain 32. The pursing strips 38*a*, 38*b* provide localised rigidity to the drain 32 and assist with the opening of the drain aperture 35, in use. Specifically, the pursing strips 38*a*, 38*b* may be squeezed laterally to arch the pursing strips 38*a*, 38*b* (and hence the inner and outer walls 18*b*, 20*b* respectively) in opposing directions to open the drain aperture 35.

Figure 2A:
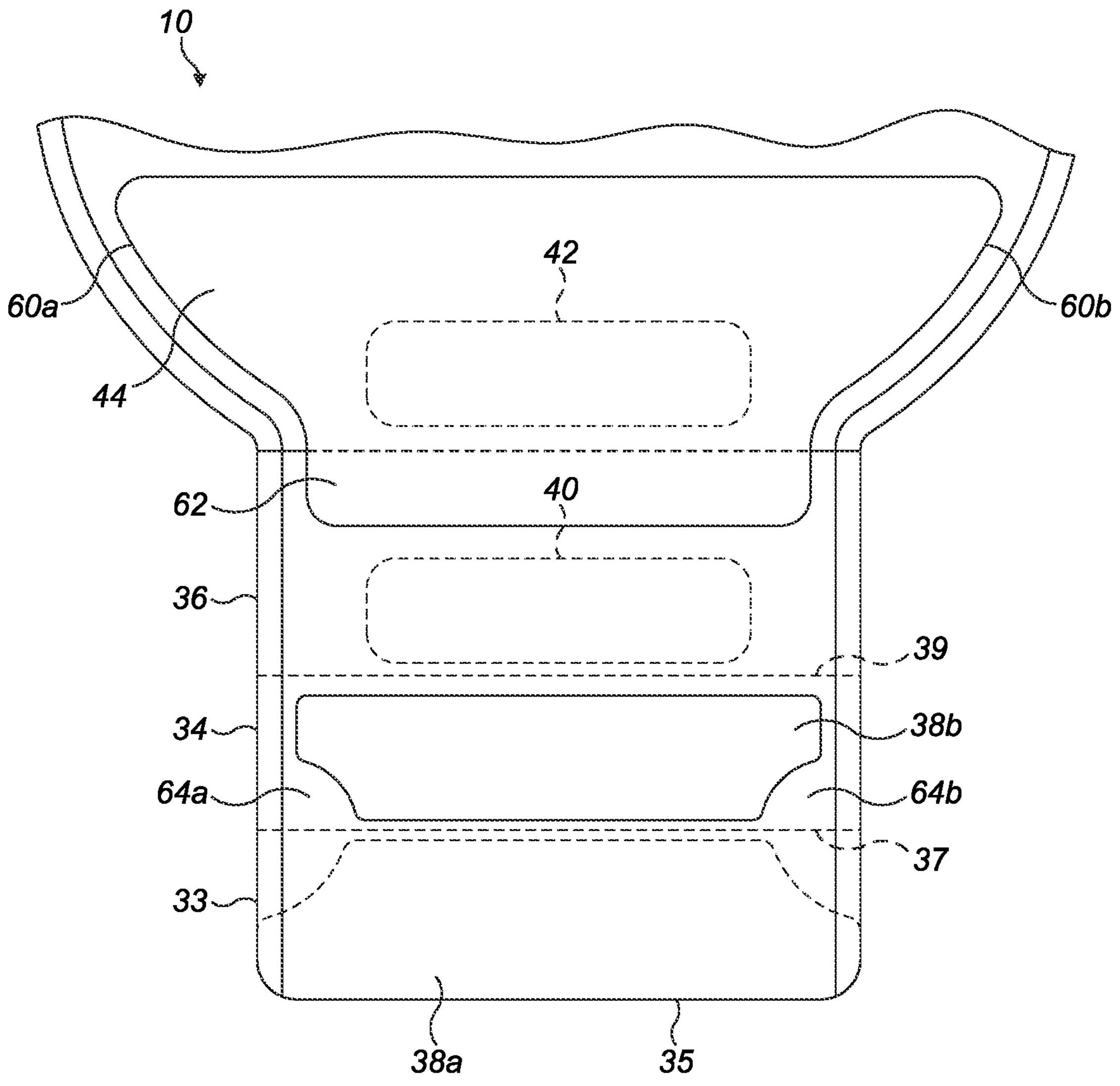
FIGS. 2A-2B are further side perspective views showing sections A and B of FIGS. 1A and 1B, respectively.

The pursing strips 38*a*, 38*b* are largely rectangular but include cut out regions at corners thereof as shown in FIGS. 1A and 2A specifically. The cut out regions of the first pursing strip 38*a* are aligned with corresponding cut out regions of the second pursing strips to form semi-circular interaction regions 64*a*, 64*b* within the drain 32. The interaction regions 64*a*, 64*b* define locations on the drain 32 which a user may interact with the open the drain aperture 35, specifically by squeezing opposing edges of the pursing strips 38*a*, 38*b* towards one another to bend or arch the strips away from one another. The user/ostomate may, in use, use a thumb and forefinger, for example, in opposing interaction regions 64*a*, 64*b* to open the drain aperture 35 by performing a pinching action.

The drain 32 includes a first fastening element in the form of a strip of hook fasteners 40 provided on an outer surface of the inner wall 18*b*. Specifically, the strip of hook fasteners 40 is provided on the outer surface of the portion of the inner wall 18*b* defining the third segment 36 of the drain 32. A corresponding second fastening element 42 is provided on a flap 44 attached (e.g. welded with the hot-melt adhesive bonding to the flap, or alternatively adhesively secured, for example using adhesive tape) to an outer surface of the outer comfort layer 20*a*. The second fastening element similarly takes the form of a strip of hook fasteners 42.

Figure 2B:
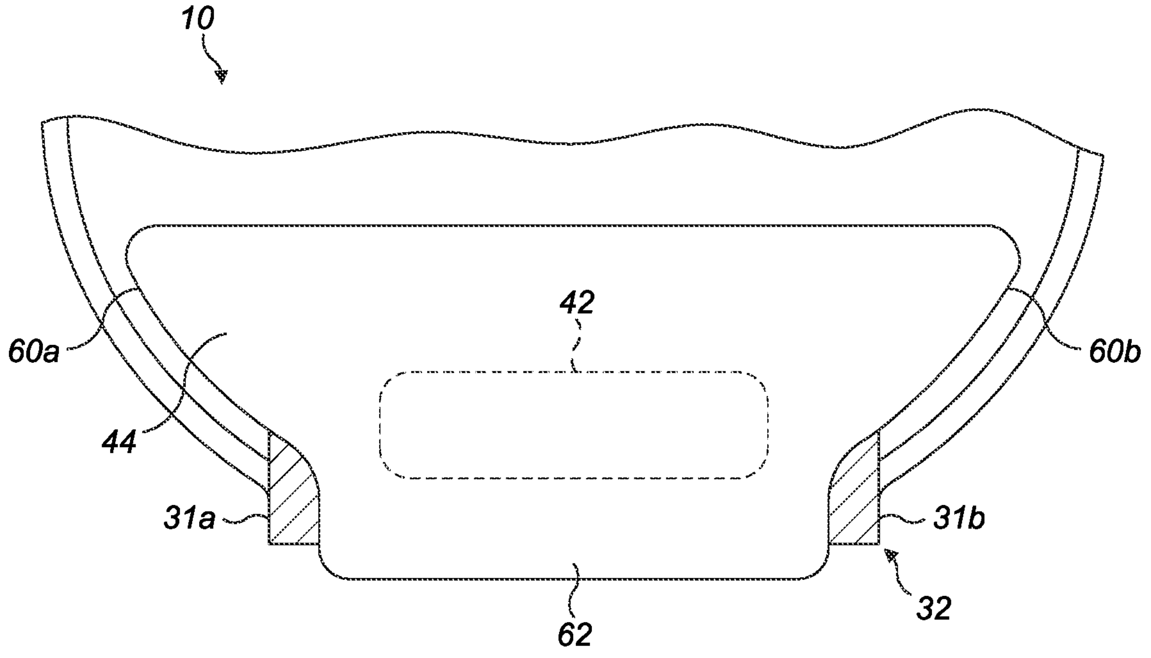
Figure 3:
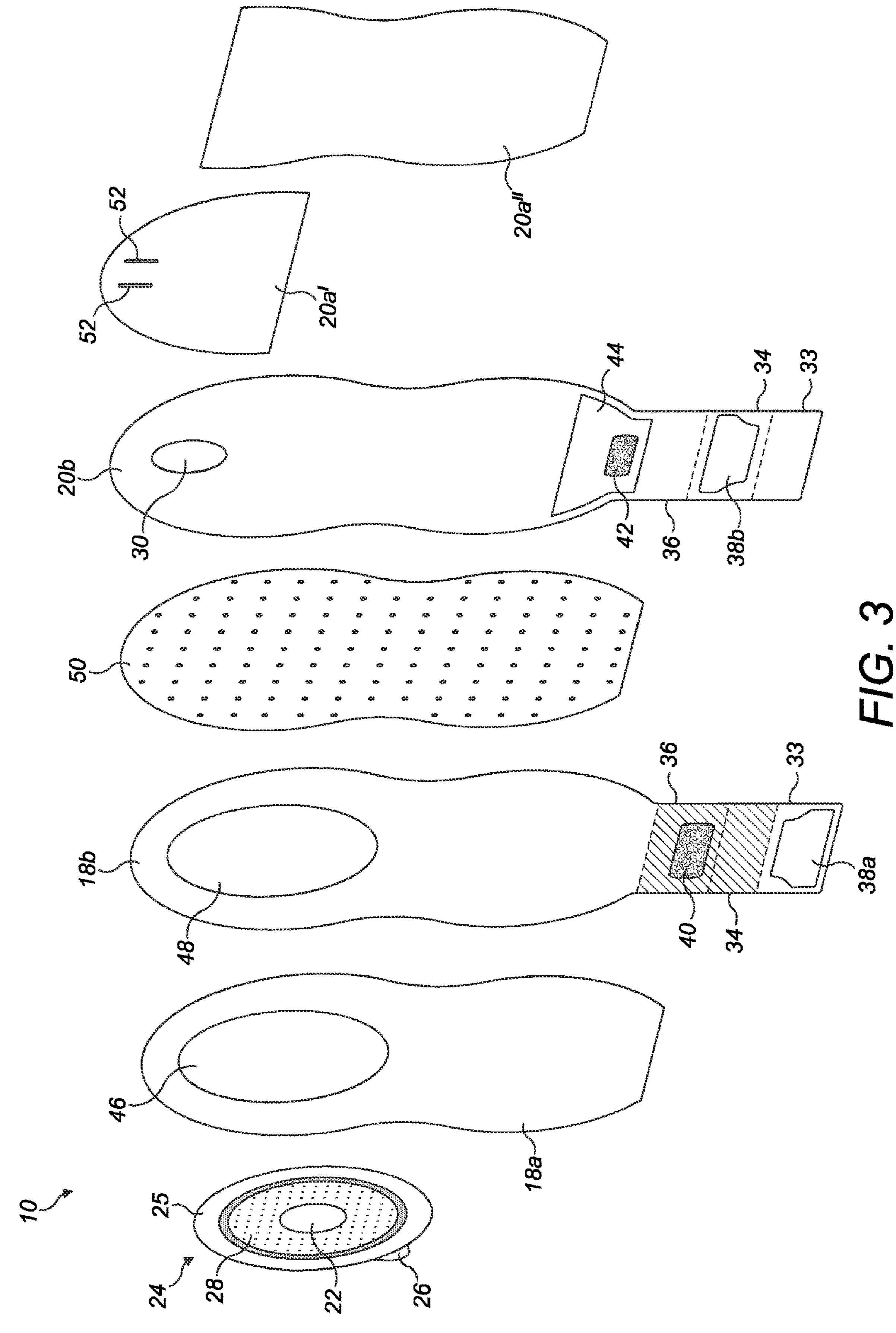
FIG. 3 is an exploded perspective view of the ostomy pouch shown in the preceding Figures.

The flap 44 extends across substantially the entire width of the pouch 10, out towards the sealed periphery of the pouch 10 as shown specifically in FIGS. 1A to 2B. The flap 44 does not overlie the sealed edge of the pouch 10 so as not to interfere with the seal, primarily so as not to interfere with the sealing process during manufacturing of the pouch 10. The flap 44 includes a pair of opposing curved edges 60*a*, 60*b* which correspond to the shape and form of the curved continuous edge of the pouch 10. This maximises the coverage of the flap 44 over the outer comfort layer 20*a*. The flap 44 is additionally provided with a flange 62 which projects from the flap 44 downwards (in the "in-use" orientation). As shown in FIGS. 1B and 2B specifically, the flange 62 is positioned to overlie a portion of the drain 32 when in the stowed position to provide greater coverage of the drain by the flap 44.

In use, the drain 32 is moved from the deployed position to the stowed position by folding the drain 32 about fold lines 37, 39 upwards and away from the ostomate, by first bringing the first segment 33 adjacent to and overlying the second segment by folding along fold line 37, and subsequently folding the folded first and second segments 33, 34 about the fold line 39 bringing those segments adjacent to and overlying the third segment 36. Finally, the drain 32 is folded once more bringing the folded drain 32 to a position where it overlies a portion of the outer comfort layer 20*a* as shown in FIG. 1B, with the flap 44 folded downwards bringing the second fastening element 42 into contact and engagement with the first fastening element 40 to retain the drain 32 in the stowed position. As shown in FIGS. 1B and 2B, in the stowed position the flap 44 does not cover the entirety of the stowed drain 32. Rather, the drain 32 is only partly covered by the flap 44, and has one or more portions which remain uncovered and thereby visible, in use. Specifically, edge regions 31*a*, 31*b* remain visible with the drain 32 in the stowed position. The edge regions 31*a*, 31*b* visible in the stowed position comprise portions of the inner wall 18*b* which, as discussed below, is opaque. This advantageously prevents the interior of the drain 32 being visible when the drain 32 is stowed.

The drain 32 is moved from the stowed position to the deployed position in the opposite manner.

As discussed herein, the drain 32 is formed from portions of the inner and outer walls 18*b*, 20*b* of the pouch 10. The portion of the inner wall 18*b* defining the drain 32 is substantially opaque. In this way, when in the stowed position with the drain 32 folded up and over itself away from the ostomate, the inner wall 18*b* forms an opaque outer surface of the folded drain 32. Together with the flap 44, and by folding the drain 32 up and over an outer surface of an opaque comfort layer 20*a*, the opaque outer surface of the drain 32 prevents the contents of the pouch 10 being visible with the drain 32 in the stowed position. This is beneficial from a user point of view where the contents of the pouch may be unsightly, and the ostomate may wish for the contents to be concealed during normal use of the pouch. At the same time, the portion of the outer wall 20*b* defining the drain 32 is transparent. In this way, when deployed, the outermost surface of the drain 32 is transparent allowing the ostomate/user to view the contents of the pouch 10, and specifically the contents passing through the drain 32 during a draining process. Advantageously, this provides greater control over the draining process.

Figure 5:
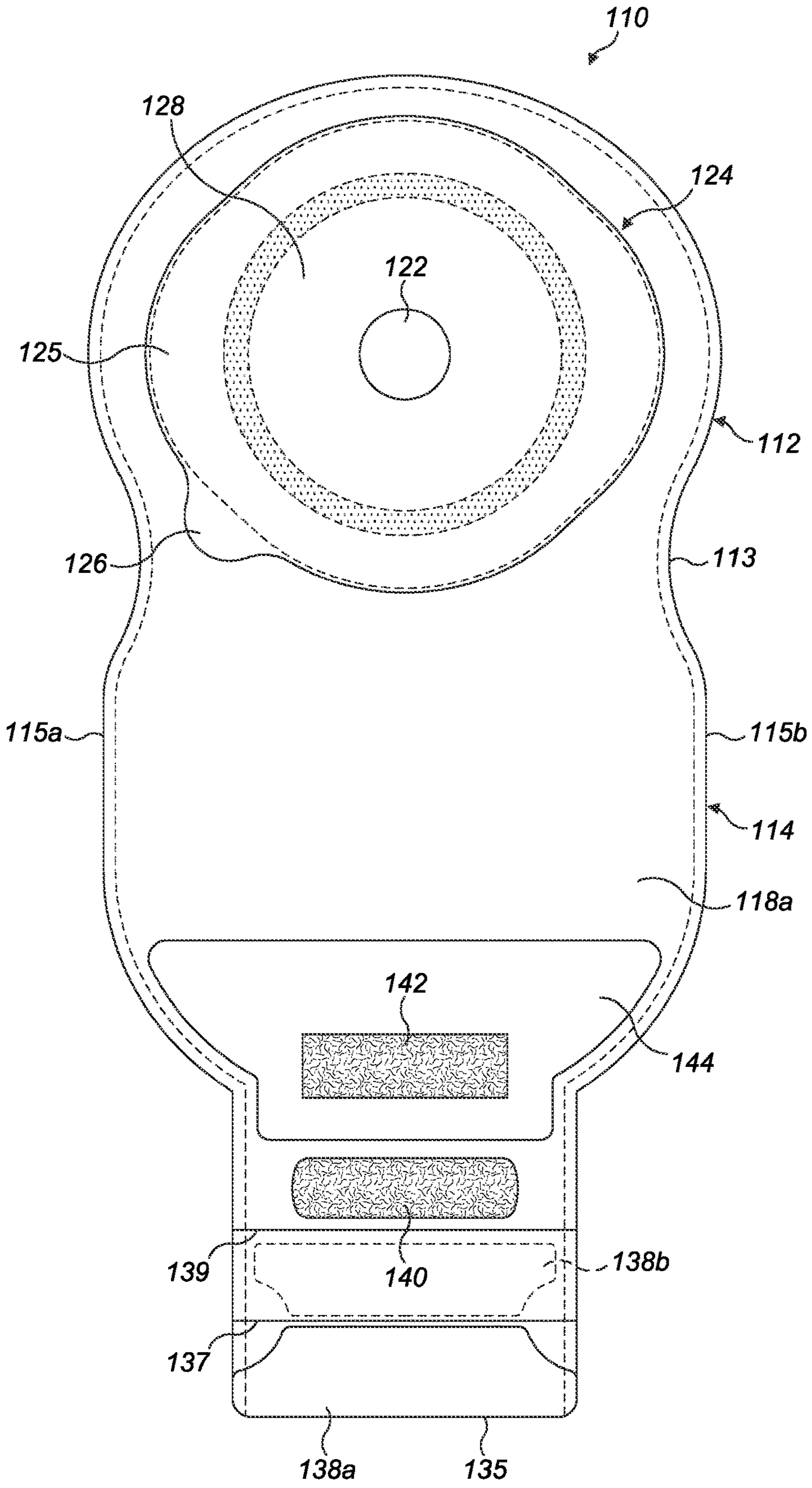
FIG. 5 is a side perspective view of a second embodiment of an ostomy pouch of the invention.

FIG. 5 illustrates a second embodiment of a pouch 110 according to the present invention.

Where the features of pouch 110 are equivalent to those of pouch 10, like reference numerals have been used. Equivalent features are configured in the same way in pouch 110 as pouch 10 described herein, unless otherwise stated herein. For features that are common, reference should be made to the preceding description also.

Pouch 110 is formed of an inner wall and an outer wall sealed about their periphery and define a cavity for containing a stomal output. Again, the cavity includes a first, upper section 112, and a second, lower section 114 which are generally rounded in shape with convex curved edges. The upper and lower sections 112, 114 are separated by a waisted section 113 which is narrower in width than upper and lower sections 112, 114. The pouch 110 is dimensioned approximately equal to the dimensions of pouch 10 discussed herein.

As with pouch 10, the inner and outer walls are formed of a flexible, plastics sheet material and are provided with inner comfort layer 118*a* and outer comfort layers formed of woven, fabric material and which overlie respective inner and outer walls. Again, a stomal inlet is provided in the upper section 112 of the pouch 110 for receiving stomal output into the cavity, with an ostomy wafer 124 located within an aperture in the inner comfort layer 118*a* and positioned over the stomal inlet, in use. The ostomy wafer 124 is configured in the same way as ostomy wafer 24 described hereinabove. The pouch similarly includes a deployable drain 132 configured in substantially the same manner as drain 32 of pouch 10. As with pouch 10, the deployable drain 132 is moveable between a deployed position (shown in FIG. 5) and a stowed position in the same manner, by folding the drain 132 about various fold lines 137, 139 and securing in position using fasteners 140, 142.

Pouch 110 differs in that the lower section 114 of pouch 110 is shaped differently, and in particular is more elongated. Here, the lower section 114 of the pouch 110 includes straight edge portions 115*a*, 115*b* extending from the waisted section 113 to define a lower section 114 which has a generally rectangular portion proximal to the waisted section 113, and a generally rounded section at a lowermost edge of the pouch 110. The elongated lower section 114 may advantageously have a greater capacity for storing stomal output therein.

Figure 6A:
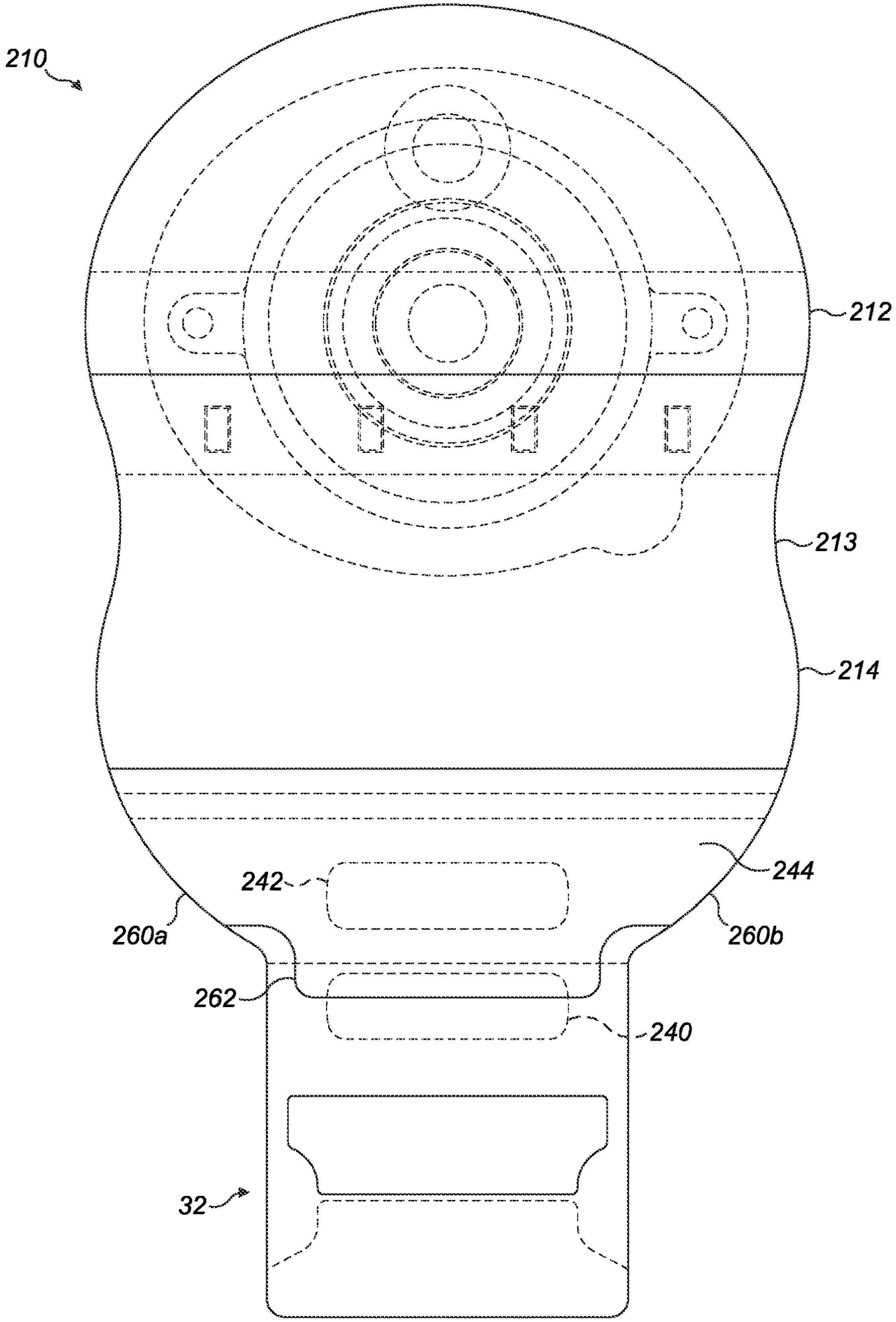
FIG. 6A is a side perspective view of a third embodiment of an ostomy pouch in accordance with the invention, illustrating a drain of the ostomy pouch in a deployed position.
Figure 6B:
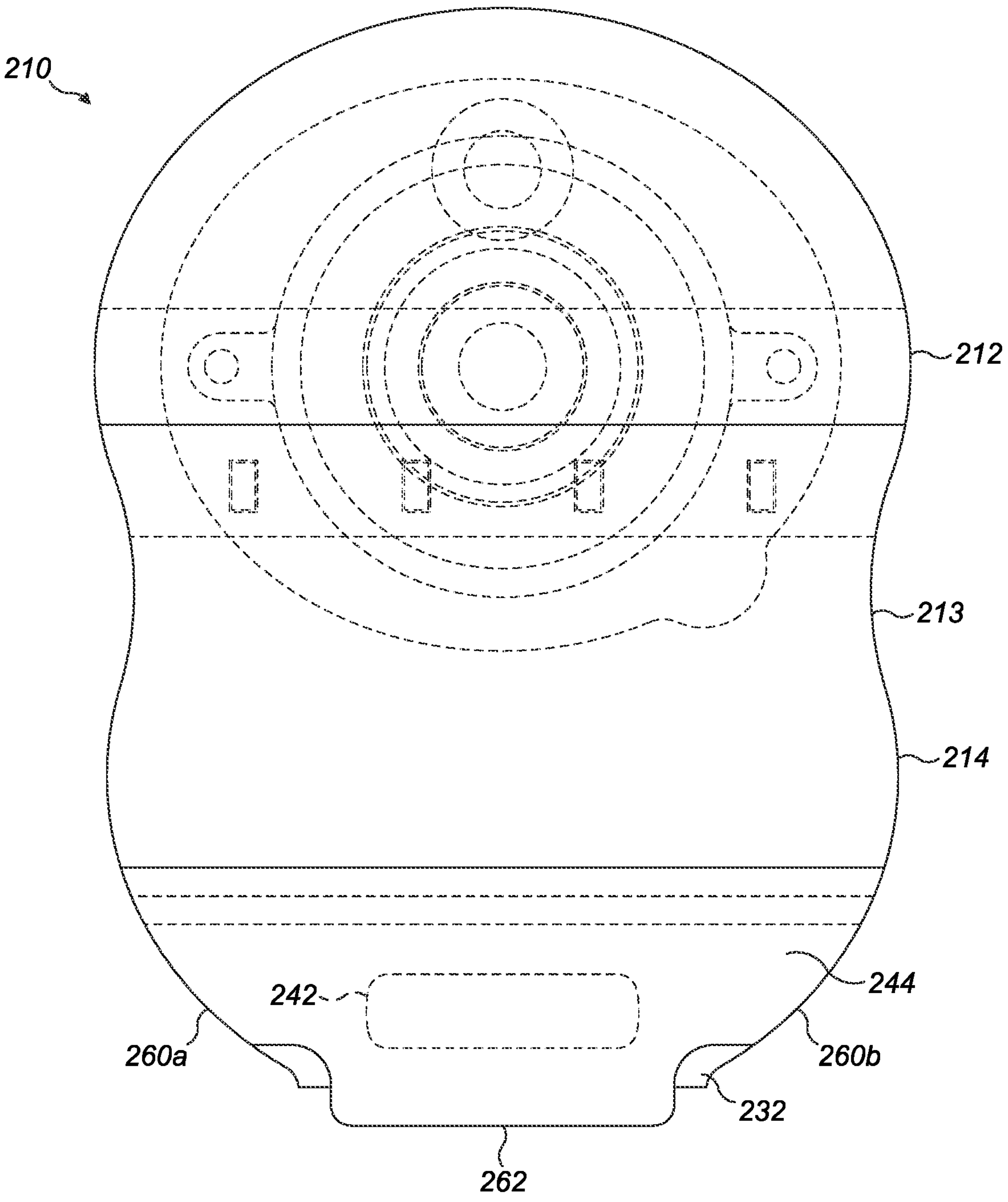
FIG. 6B is a further side perspective view of the ostomy pouch of FIG. 6A, illustrating the drain in a stowed position.
Figure 7:
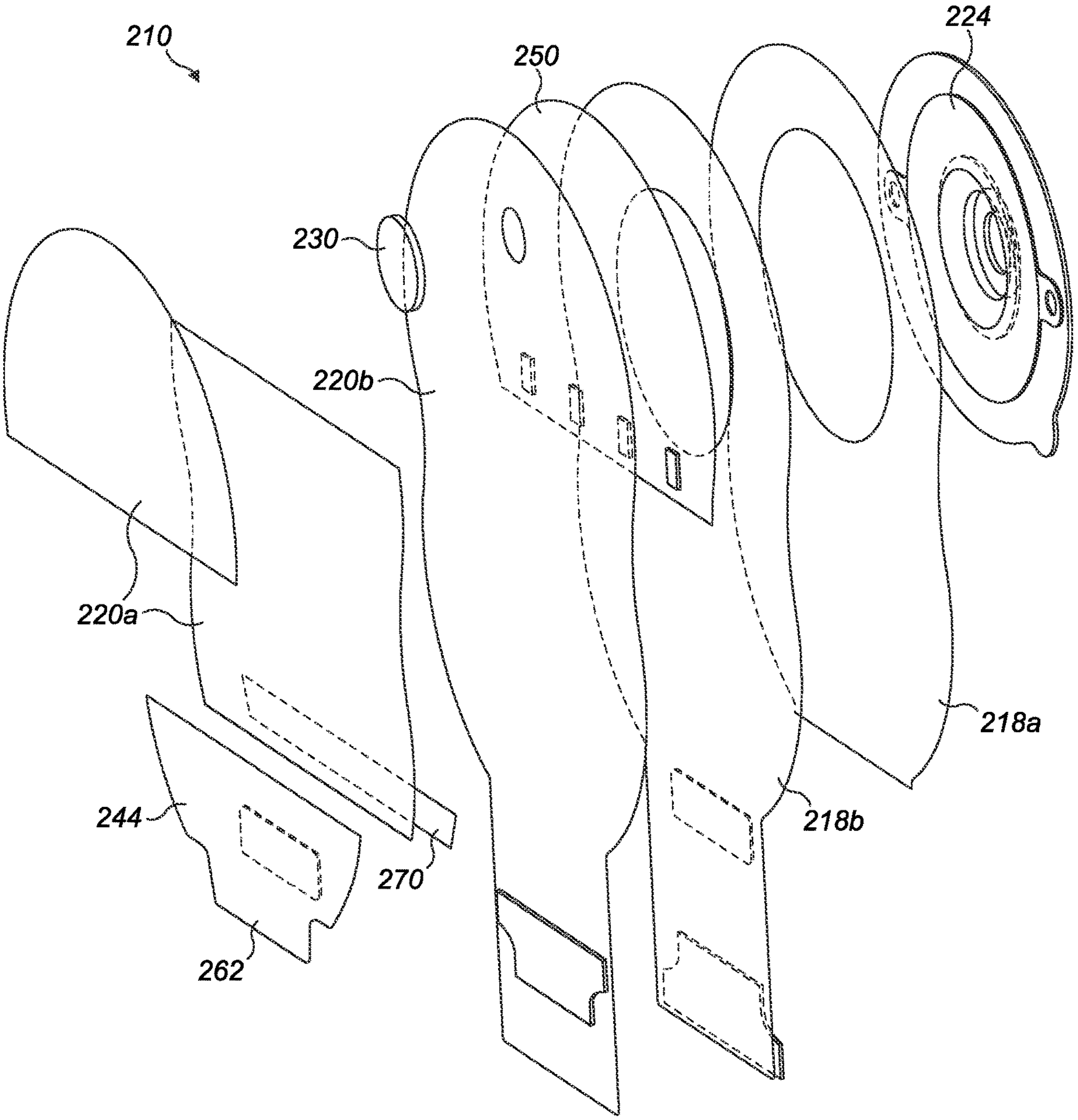
FIG. 7 is an exploded perspective view of the ostomy pouch shown in FIGS. 6A and 6B.

FIGS. 6A, 6B and 7 illustrate a third embodiment of a pouch 210 according to the present invention.

Where the features of pouch 210 are equivalent to those of pouch 10, like reference numerals have been used. Equivalent features are configured in the same way in pouch 210 as pouch 10 described herein, unless otherwise stated herein. For features that are common, reference should be made to the preceding description also.

Pouch 210 is formed of an inner wall and an outer wall sealed about their periphery and define a cavity for containing a stomal output. Again, the cavity includes a first, upper section 212, and a second, lower section 214 which are generally rounded in shape with convex curved edges. The upper and lower sections 212, 214 are separated by a waisted section 213 which is narrower in width than upper and lower sections 212, 214. Whilst similar in shape, the pouch 210 of the third embodiment is somewhat squatter than that of the embodiments discussed above, with a "standard" sized length of 194 mm when the drain is stowed and 256 mm when the drain is deployed, (a "large" size is envisaged with a shape similar to that of the second embodiment and a length of 224 mm stowed, and 286 mm with the drain deployed). Another difference in terms of shape is that the waist curvature radii in this example is 60 mm. Of course those skilled in the art will have no trouble determining suitable alternative sizes and shapes.

As with pouch 10, the inner and outer walls 218*b*, 220*b* are formed of a flexible, plastics sheet material and are provided with inner comfort layer 218*a* and outer comfort layers 220*a* formed of woven, fabric material and which overlie respective inner and outer walls. Again, a stomal inlet is provided in the upper section 212 of the pouch 210 for receiving stomal output into the cavity, with an ostomy wafer 224 located within an aperture in the inner comfort layer 218*a* and positioned over the stomal inlet, in use. The ostomy wafer 224 is configured in the same way as ostomy wafer 24 described hereinabove. The pouch similarly includes a deployable drain 232 configured in substantially the same manner as drain 32 of pouch 10. As with pouch 10, the deployable drain 232 is moveable between a deployed position (shown in FIG. 6A) and a stowed position (shown in FIG. 6B) in the same manner, by folding the drain 232 about various fold lines and securing in position using fasteners 240, 242.

In addition to the different size, the pouch 210 of the third embodiment differs in that it does not include a separation filter extending the length of the pouch, but rather just a separation panel 250 provided between the inner and outer walls 218*b*, 220*b*, in the top half of the pouch, to avoid waste blocking the filter 230 through which stomal gas is vented. It also does not include slits in the outer comfort layers 220*a*, with gas instead escaping through the gap between the upper and lower comfort layers 220*a*.

However, the most notable difference in terms of the invention is that in this third embodiment, the flap 244 on which one of the fasteners 242 is provided extends across the entire width of the pouch 210, out to the sealed periphery of the pouch 210 as shown specifically in FIGS. 6A, 6B and 7. The flap 244 does overlie the sealed edge of the pouch 210 and is attached after the sealing process during manufacturing of the pouch 210 by means of an adhesive, in this embodiment provided as an adhesive tape. The flap 244 includes a pair of opposing curved edges 260*a*, 260*b* which correspond not only to the shape and form of the curved continuous edge of the pouch 210, but also to the width and position of the curved continuous edge of the pouch. This both maximises the coverage of the flap 244 over the outer comfort layer 220*a*, but also provides a neat outline to the pouch. The flap 244 is provided with a flange 262 which projects from the flap 244 downwards (in the "in-use" orientation) to overlie a portion of the drain 232 when in the stowed position to provide greater coverage of the drain by the flap 244.

In use, the drain 232 is moved in exactly the same way as the first embodiment and as in the first embodiment (as shown in FIGS. 6B and 6B in respect of this third embodiment), in the stowed position the flap 244 does not cover the entirety of the stowed drain 232, leaving edge regions visible in the stowed position, with these edge regions of course comprising portions of the inner wall 218*b* which is opaque. This advantageously prevents the interior of the drain 32 being visible when the drain 32 is stowed.

The one or more embodiments are described above by way of example only. Many variations are possible without departing from the scope of protection afforded by the appended claims.

The invention claimed is:

1. An ostomy pouch, comprising:

inner and outer walls of flexible sheet material sealed about a periphery thereof to define:

a cavity for containing a stomal output; and a deployable drain for draining stomal output from the cavity;

a substantially opaque comfort layer provided, at least in part over an outer surface of the inner and/or outer walls of the flexible sheet material; and a fastener arrangement configured to retain the deployable drain in the stowed position, the fastener arrangement comprising a first fastener located on an outer surface of the comfort layer and a second fastener provided on the inner wall or outer wall of the ostomy pouch;

wherein the deployable drain is moveable between a deployed position for draining the stomal output from the cavity and a stowed position for storage of the deployable drain, with at least part of the drain overlying a portion of the comfort layer in the stowed position;

wherein at least a portion of the inner wall defining the deployable drain is opaque and at least a portion of the outer wall defining the deployable drain is at least partly transparent;

wherein the first fastener comprises a flap which is secured to the comfort layer;

wherein the flap is provided on the comfort layer overlying an outer wall of the pouch, away from the ostomate, in use, and extends across substantially the entire width of the ostomy pouch, out towards a sealed periphery of the ostomy pouch;

wherein the flap is provided with a flange projecting downwards from the flap and positioned to overlie a portion of the deployable drain when in the stowed position, the flange being an outermost layer when the deployable drain is in the stowed position; and wherein the pouch comprises one or more curved edges, and the flap is similarly curved to correspond the shape and form of the curved edge(s) of the pouch.

2. An ostomy pouch of claim 1, wherein the drain comprises an elongate extension of the inner and outer walls, extending from a drain inlet at the cavity and a drain aperture at a distal end of the drain channel through which stomal output from within the cavity can be drained from the pouch.

3. An ostomy pouch as claimed in claim 1, wherein the deployable drain is moveable between stowed and deployed positions by rolling or folding the drain and wherein the drain is moveable, in use, from the deployed position to the stowed position by folding and/or rolling the drain in a direction which is upwards and away from the ostomate.

4. An ostomy pouch as claimed in claim 1, wherein the second fastener is located on a portion of the inner wall of the pouch at least partly defining the drain.

5. An ostomy pouch as claimed in claim 1, wherein the drain comprises a pair of pursing strips, each strip being fixed to the inner or outer wall of the pouch.

6. An ostomy pouch as claimed in claim 1, wherein the drain is sub-divided into two or more segments defined by fold lines about which the drain may be folded when moving between deployed and stowed positions, wherein the drain segments are sequentially folded to overlie one another in moving from the deployed position to the stowed position.

7. An ostomy pouch as claimed in claim 6, wherein the drain is sub-divided into three segments, with a first pursing strip positioned on the inner wall of the pouch and defining, at least in part a first segment of the drain, a second pursing strip positioned on the outer wall of the pouch and defining, at least in part a second segment of the drain, and with the second fastener provided on the inner wall of the pouch and defining, at least in part, a third segment of the drain.

8. An ostomy pouch as claimed in claim 1, wherein at least a portion of the deployable drain is visible to a user wearing the ostomy pouch when the deployable drain is in the stowed position.

9. An ostomy pouch as claimed in claim 1, wherein at least a portion of the deployable drain is visible to a user wearing the ostomy pouch when the deployable drain is in the stowed position and wherein in the stowed position the deployable drain is partly covered by the flap, but also has one or more portions which remain uncovered and thereby visible, in use.

10. An ostomy pouch as claimed in claim 9, wherein the or each portion visible in the stowed position comprises a region or regions of the drain at or proximal to one or more edges.

11. An ostomy pouch as claimed in claim 10, wherein the or each portion visible in the stowed position comprises a portion of the opaque inner wall of the pouch defining the drain.

12. An ostomy pouch as claimed in claim 1, wherein the pouch comprises an inner comfort layer and an outer comfort layer, the inner comfort layer overlying at least a portion of the inner wall of the pouch and the outer comfort layer overlying at least a portion of the outer wall of the pouch.

13. An ostomy pouch as claimed in claim 12, wherein the inner comfort layer and the outer comfort layer do not overlie the inner or outer walls of the pouch at the portions of the inner and/or outer walls which define the drain.

14. An ostomy pouch as claimed in claim 1, wherein the cavity comprises an upper section, a lower section, and a waisted section located between the upper and lower sections, wherein the waisted section comprises a minimum width which is less than the maximum width of the upper and/or lower sections.

15. An ostomy pouch according to claim 6 wherein the flap extends up to the seal about the periphery of the pouch.

16. An ostomy pouch according to claim 6 wherein the flap extends across the entire width of the pouch, right to the edge of the pouch.

17. As ostomy pouch as claimed in claim 1, wherein the flap is wider than the deployable drain.

* * * * *